(12) United States Patent
Ritter et al.

(10) Patent No.: US 7,465,463 B2
(45) Date of Patent: *Dec. 16, 2008

(54) COMPOSITIONS COMPRISING MICROSPHERES WITH ANTI-INFLAMMATORY PROPERTIES FOR HEALING OF OCULAR TISSUES

(75) Inventors: Vladimir Ritter, Kiryat Yam (IL); Marina Ritter, Kiryat Yam (IL); Mark Tendler, Haifa (IL); Lev Feitelberg, Nesher (IL)

(73) Assignee: Polyheal, Ltd., Nesher (IL)

( * ) Notice: Subject to any disclaimer, the term of this patent is extended or adjusted under 35 U.S.C. 154(b) by 469 days.

This patent is subject to a terminal disclaimer.

(21) Appl. No.: 10/234,274

(22) Filed: Sep. 4, 2002

(65) Prior Publication Data

US 2004/0043075 A1    Mar. 4, 2004

(51) Int. Cl.
*A61K 9/16* (2006.01)
(52) U.S. Cl. ........................ 424/497; 424/491
(58) Field of Classification Search ............... 424/78.1
See application file for complete search history.

(56) References Cited

U.S. PATENT DOCUMENTS

| | | | | |
|---|---|---|---|---|
| 5,506,280 A | * | 4/1996 | Miller et al. | 523/218 |
| 5,837,226 A | * | 11/1998 | Jungherr et al. | 424/78.1 |
| 5,861,149 A | * | 1/1999 | Ritter | 424/78.06 |
| 6,007,845 A | * | 12/1999 | Domb et al. | 424/501 |
| 6,086,863 A | * | 7/2000 | Ritter et al. | 424/78.06 |
| 6,491,903 B1 | * | 12/2002 | Forster et al. | 424/78.01 |
| 6,548,302 B1 | * | 4/2003 | Mao et al. | 435/455 |

* cited by examiner

*Primary Examiner*—Jyothsna A Venkat
(74) *Attorney, Agent, or Firm*—Browdy and Neimark, P.L.L.C.

(57) ABSTRACT

The present invention relates to compositions of microspheres suitable for application to ocular injuries and inflammation, and to methods of use of the compositions alone or in combination with other agents in the prevention and treatment of ocular injuries and inflammation. The compositions, which increase the rate of healing, can be used to treat injuries and inflammation, including but not limited to those caused by foreign bodies, infections, burns, lesions, lacerations, ischemia, injuries from blunt trauma, traumatic hyphema, sympathetic ophthalmia, injuries from radiant energy, cataracts, corneal erosions or optic nerve injuries, and in procedures such as post-trabeculectomy (filtering surgery), post pterygium surgery; post ocular adnexa trauma and surgery, post intraocular surgery, post vitrectomy, post retinal detachment or post retinotomylectomy.

4 Claims, 2 Drawing Sheets

COMPOSITIONS COMPRISING MICROSPHERES WITH ANTI-INFLAMMATORY PROPERTIES FOR HEALING OF OCULAR TISSUES

1. FIELD OF THE INVENTION

The present invention relates to compositions of microspheres having wound healing capacity with anti-inflammatory properties for application to ocular inflammation or injuries, and to methods of use of said composition alone or in combination with other agents in the prevention and treatment of ocular inflammation or injuries.

2. BACKGROUND TO THE INVENTION

The eye has a series of defenses against infection and injury, beginning with the skin of the eyelid, which is an effective barrier to microbes and other foreign bodies. The conjunctiva, which borders the cornea, is a mucous membrane designed to trap foreign particles and keep the eye moist. The corneal epithelium has two mechanisms of protection. The tight junctions of the base of corneal epithelium that prevents the penetration of fluids, and the surface of the corneal epithelium smoothed by a continuous liquid flash of the tear layers that prevents the adherence of microorganisms. The evaporation of tears from the surface of the eye lowers the ocular surface temperature to inhibit microbial growth, and blinking sweeps away microorganisms. These and other mechanisms to prevent infection and injury, however, can be rendered largely ineffective by inflammation or injury to the eye. Even a minor injury can disrupt the epithelial surfaces of the eye, providing a place for microorganisms to adhere and colonize.

Eye injuries are common and can be caused in numerous ways, including, blunt trauma from a sports injury, a foreign object such as a shard of metal or glass, lacerations from sharp objects, and chemical or thermal burns. Treatment often involves removal of any foreign bodies, rinsing of the eye to dilute chemicals, suturing of lacerations, and application of topical antibiotics. Injuries may or may not be patched, since patching sometimes promotes microbial growth by raising the ocular surface temperature, making conditions more favorable to microbes. It is important for eye injuries to be healed as quickly as possible to reduce the risk of infection.

Ocular inflammation is a nonspecific result of tissue damage. While there are several agents that can elicit an inflammatory response, microbial (bacterial, viral, or fungal) infection and various immune conditions (e.g., hypersensitivity, allergy, and autoimmunity) are the most common causes of ocular inflammation. Inflammation associated with chemical and thermal injury can have a highly destructive outcome on the eye, and especially the cornea. Physical trauma to the cornea may-be accompanied by intraocular inflammation, synechiae leading to glaucoma, and secondary membrane formation.

Complications may arise during the healing process of an ocular injury. If the epithelialization of the cornea is incomplete one week after the injury occurred, there is a danger of stromal necrosis. In some cases there is danger of secondary hemorrhage, tissue damage by oxygen free radicals, or scarring. The rate of healing of an eye injury may be slowed in patients who have complicating factors such as, but not limited to, diabetes or old age.

The primary problem associated with topical applications of compositions to the eye is that the human eye is a very sensitive organ and any substance which is not compatible causes irritation and pain. This evokes blinking and reflex-tearing, which is a physiological reaction intended for removal of the irritating substance from the ocular surface. Irritation is a major cause of poor patient compliance with many compositions intended for ophthalmic administration. This phenomenon is aggravated by the need to include relatively high concentrations of a drug in such ophthalmic compositions in order to obtain a therapeutic effect, since bioavailability of topically applied ophthalmic drugs is generally very poor. Thus, there is no doubt that a reduction in the irritating effect of a composition will enable increased ocular drug bioavailability, increased patient compliance with the drug, and enhanced therapeutic efficacy of the drug.

Aqueous solutions are by far the most common vehicles for ophthalmic drugs, however the ocular bioavailability of drugs administered thereby is generally very poor due to rapid drainage and tear turnover. See Fitzgerald et al. (1987) J. Pharm. Pharmacol. 39:487-490. A typical dose of ophthalmic solution is in the range of about 50-100 µl, which far exceeds the normal lachrymal volume of about 7-10 µl. Thus, the portion of the dose that is not eliminated by spillage from the palpeberal fissure is quickly drained. Furthermore, lacrymation and physiological tear turnover, which in humans is about 16% per minute under normal conditions, increases after the introduction of the ophthalmic composition, resulting in rapid dilution of the remaining amount of drug that has not been spilled or drained. As a consequence, the contact time with the absorbing surfaces of the eye (i.e., the cornea and sciera) of drugs which are applied to the eye via liquid aqueous compositions is less than about two minutes.

Attempts have been made to develop various delivery vehicles in which the drug residence time in the eye is increased. The most direct approach for achieving this goal is by an increase in the viscosity of the vehicle. Thus, various viscous vehicles, such as hydrogels or ointments, have been attempted, some of which also enable delivery of hydrophobic drugs into the eye. Additionally, many attempts to use various non-conventional carriers, such as liposomes, micellar solutions and nano-particles, as vehicles of ophthalmic drugs have also been made. Such delivery systems may provide limited success in prolonging the residence time of drugs in the eye and hence some enhancement of the ocular bioavailability. See Harmia et al. (1987) Pharm. Acta Helv. 62:322-332. Saettone et al. (1988) J. Pharm. 43:67-70 and Meisner et al. (1989) Int. J. Pharm. 55:105-113. Emulsions have also been suggested as vehicles for delivery of drugs to the eye in references such as EP 391,369, Ellis et al. (1987) J. Ocular Pharmcol. (U.S.) 3:121-128, and Shell (1984) Surv. Ophthalmol. 29:177-178.

Among the many types of drugs commonly administered for prevalent ophthalmic indications are the anti-inflammatory steroids. These agents suffer from the drawback that they are known to elevate intraocular pressure and that they may directly or indirectly interfere with wound healing.

Topical steroids such as corticosteroids are commonly used for anti-inflammatory therapy of the eye, especially for treating inflammatory conditions of the palpebral or bulbar conjunctiva, cornea anterior and posterior segments of the globe. Common therapeutic applications for steroids include autoimmune, allergic and viral types of conjunctivitis, acne rosacea, superficial iritis, indo-cyclitis, as well as posterior segment inflammatory processes like uveitis. Steroids also are used to ameliorate inflammation associated with corneal injury due to chemical or thermal burns, or penetration of foreign bodies. Such conditions may result from surgery, injury, allergy or infection to the eye and can cause severe discomfort.

Numerous therapies and therapeutic agents have been developed over the years to treat sequelae of ocular degeneration, physical and chemical traumatic ocular injury, and ocular inflammation. While many of these have proven to be useful and provide an acceptable level of therapy to the damaged eye tissue, others have unacceptable side effects that dispose the already impaired/injured eye to further vulnerability (e.g., toxicity).

Despite their therapeutic advantages, topical ocular use of corticosteroids is associated with a number of complications, including elevation of intraocular pressure, posterior subcapsular cataract formation, secondary ocular infection, retardation of corneal wound healing, uveitis, mydriasis, transient ocular discomfort and ptosis. Numerous systemic complications also may arise from the topical ocular application of corticosteroids. These complications include adrenal insufficiency, Cushing's syndrome, peptic ulceration, osteoporosis, hypertension, muscle weakness or atrophy, inhibition of growth, diabetes, activation of infection, mood changes and delayed wound healing.

Many antibiotics (e.g., beta-lactams and certain fluoroquinolones) are not well-tolerated, give rise to toxicities, or are of moderate efficacy. The use of immunosuppressive agents in treating autoimmune ocular disease, e.g., uveitis, is controversial because of many serious side effects including bone marrow depression, thrombocytopenia, bleeding, nausea, vomiting, and stomatitis occur. Without attempting a comprehensive and exhaustive list of agents that have proven beneficial in the management of primary and secondary sequelae of ocular degeneration, injury, surgical trauma, and attendant inflammation, representative classes of compounds include antibacterials (e.g., broad spectrum antibiotics), antivirals, non-steroidal antiinflammatory agents (NSAIDs), aminosteroids, collagenase inhibitors, cholinergics, cycloplegics, and wound healing modulators.

The inventor has described that microspheres can be used to enhance healing in certain types of wounds, including diabetic ulcers in humans (U.S. Pat. No. 5,861,149) and that patent is incorporated in its entirety in this application. The present invention relates to the use of these microspheres for ocular management after discovering that the microspheres compositions possess wound healing capacity with anti-inflammatory properties In accordance with the present invention, effective means for enhancing wound healing while at the same time reducing the accompanying inflammatory process of the eye (without the need for anti-inflammatory medication such as steroids and NSAIDs) is provided for the first time and thereby a long felt need has been fulfilled.

3. SUMMARY OF THE INVENTION

It is an object of the present invention to provide a composition that can treat or prevent ocular injury or promote the healing of ocular tissues when applied to an injured eye.

It is an object of the present invention to provide a composition that can treat or prevent inflammation and inflammatory responses and promote the healing of ocular tissues when applied to an inflamed eye and shorten the time of preparation of a damaged eye for surgery.

It is another object of the present invention to provide a composition that serves as a medium for a suspension of microspheres and a drug delivery system for pharmaceutical agents.

It is yet another objective of the present invention to provide a composition that will prevent scar formation in the eye.

It is yet another objective of the present invention to provide a composition that will serve to promote cellular fusion in the eye.

It is yet another objective of the present invention to provide a composition that will reduce inflammatory responses thereby preventing scarring while facilitating ocular healing.

It is yet another objective of the present invention to provide a composition including microspheres and an exogenous growth factors added to it that will promote ocular injury healing.

It is yet another objective of the present invention to provide a composition including microspheres with or without an active substance, which is applied as adjunct therapy to surgery, radiation therapy, or chemotherapy.

It is yet another objective of the present invention to provide a composition including microspheres and an known active therapeutic agent selected from the group consisting of: antibiotics; vitamins; minerals; anticancer agents; antiviral agents; antifungal agents; an analgesic or anesthetic; a sulfonamide; agents to reduce intraocular pressure, including but not limited to timolol, epinephrine, and acetazolamide; proteolytic enzymes to prevent stromal necrosis; other agents including but not limited to acetylcysteine, penicillamine, and ethylenediaminetetra-acetic acid (EDTA); bradykinin antagonists combined with 21-aminosteroids; cycloplegic agents; antioxidants; anti-inflammatory agents including but not limited to methylprednisolone and non-steroid anti inflammatory drugs.

It is yet another objective of the present invention to provide a composition including microspheres for use in conjunction with any invasive or non-invasive treatment to prevent the development of inflammatory reaction caused by any of the above listed factors, ocular inflammation, wound healing or post surgical eye rehabilitation.

It is yet another objective of the present invention to provide a composition including microspheres for prophylactic treatment of the eye prior to surgery.

It is yet another objective of the present invention to provide a composition including microspheres for treatment of post-trabeculectomy (filtering surgery), post pterygium surgery, post ocular adnexa trauma and surgery, post intraocular surgery and specifically, post vitrectomy, post retinal detachment and post retinotomy/ectomy.

These and other objectives are met by the compostions and methods disclosed herein.

Unexpectedly, during evaluation of the safety and efficacy of these microspheres for ocular applications, it was discovered that these suspensions of microspheres possess notable anti-inflammatory properties. It is therefore contemplated that in addition to the utility of the microspheres in promoting wound healing processes they are useful in suppressing development of the inflammatory phenomena.

The anti-inflammatory attributes of the microsphere preparations may be used for applications involving inflammation whether or not such inflammatory process is consequent to ocular injury.

The microsphere compositions are particularly useful in treating ocular injury where it is important to suppress inflammatory processes without impairing wound healing processes, as is known to occur consequent to the use of anti-inflammatory steroids.

In accordance with the present invention, the composition comprises microspheres having charged surface groups, wherein the charge can be negative or positive, said composition having a pH between about 7-9. The microsphere material is selected from the group consisting of polystyrene, derivatized polystyrene, polymethylmethacrylate (PMMA), silicone, polylysine, and poly-N-ethyl-4-vinylpyridinium bromide. According to certain embodiments of the present invention, the charged surface groups are selected from the charged groups consisting of polystyrene, derivatized polystyrene, sulfate, poly-N-ethyl-4-vinylpyridinium bromide, protamine, protamine sulfate, protamine salts, polylysine and carboxyl. Also preferably, the microsphere has a diameter in a range of from about 0.01 microns to about 200 microns, more preferably in a range of from about 1 to about 100 microns, and most preferably from about 2 to about 20 microns. According to another embodiment of the present invention, the composition also includes a pharmaceutically acceptable carrier for the microsphere.

In accordance with the present invention the composition includes a pharmaceutically acceptable carrier suitable for forming a liquid preparation, comprising saline or other pharmaceutically acceptable vehicles. In order to increase residence time of the composition in the eye it is possible to increase the viscosity of the medium by various additives as is known in the art.

In accordance with the present invention the composition for treating ocular injuries includes microspheres capable of forming a multipoint contact with a cellular membrane and a pharmaceutically acceptable carrier in which the microspheres are substantially insoluble, and a container for holding the composition. The carrier is preferably an aqueous medium.

In accordance with the present invention there is provided a container holding a composition of microspheres in aseptic condition and capable of forming multipoint contacts with a cellular membrane.

In accordance with the present invention there is provided a container holding an aseptic composition of microspheres and one or more additional active substances.

In accordance with the present invention there is provided a container holding an aseptic composition of microspheres and one or more further containers, each holding a preparation of an active substance, which can be mixed with the microspheres prior to application to the injury, or which can be applied separately to the injury.

4. BRIEF DESCRIPTION OF THE DRAWINGS

A more complete understanding of the present invention and the attendant advantages and features thereof will be more readily understood by reference to the following detailed description when considered in conjunction with the accompanying drawings wherein Polyheal1 was applied immediately after a chemical and:

5. DETAILED DESCRIPTION OF THE INVENTION

Figure 1:
FIG. 1 shows the test rabbit eye on the fourth day after the chemical burn was induced. The test rabbits were treated with Polyheal1.

The present invention relates to prophylactic and therapeutic compositions and a method for promoting the healing of ocular injuries by using microspheres. Unexpectedly, microspheres of the size range described herein promote the healing of ocular injury without the further addition or inclusion of any drug or therapeutic substance. As described below, the microspheres do not degrade or undergo other chemical alteration to produce their therapeutic effect. The microspheres of the present invention can also be administered as adjuvant therapy to conventional therapies such as radiation or laser therapy.

Surprisingly it is now disclosed for the first time that microspheres of the invention possess effective anti-inflammatory properties, as assessed by standard eye irritation tests. Therefore the microspheres have utility in the treatment of inflammation in indications unrelated to injuries to the eye.

The structure of these microspheres includes a core material and at least one type of charged surface group present at least on the exterior of the microsphere. Examples of materials include long-chain polymers such as polystyrene, latex, poly-$\beta$-alanine, polymethlylmethacrylate (PMMA), silicone, and derivatized polystyrene. Examples of surface groups include sulfate, poly-N-ethyl-4-vinylpuridinium bromide, protamine, protamine sulfate, protamine salts, polylysine, carboxyl and polystyrene. These surface groups may be present as part of the core material or may be added later by such chemical processes as derivatization of the long-chain polymer. Hereinafter the term "derivatization" refers to the process of chemically altering, modifying, or changing a molecule or a portion thereof. The microspheres produced from the polymer should be substantially insoluble in aqueous media, forming a suspension or dispersion in such media.

In order to further clarify the parameters of the present invention, a number of terms should be defined. Hereinafter, the term "injury" refers to any injury of the eye including, but not limited to, foreign bodies in any part of the eye, including shards of metal and glass, lacerations, injuries caused by blunt trauma, chemical or thermal burns, sympathetic opthalmia (diffuse inflammation of the uveal tract), traumatic hyphema, injuries caused by radiant energy such as radiant cataract, injuries sustained during medical procedures, chronic or hereditary conditions, injuries from microbial infections, corneal erosions, and nutritional and toxic optic neuropathies. Hereinafter, the term "subject" refers to a human mammal or lower animal on whom the present invention is practiced. Hereinafter, the term "promoting" includes accelerating and enhancing. Although the discussion below refers to specific types of microspheres, this is not intended to be limiting in any way. It will be appreciated to those skilled in the art that these microspheres can be beads, particles, or globules, which are either solid or hollow. In preferred embodiments of the present invention, these microspheres are dispersed in a pharmaceutically acceptable carrier medium in which the agents are substantially insoluble, for example as a suspension in an aqueous medium. The shape of the microspheres can be regular, such as spherical or elliptical, or regular non-spherical shapes; or the shape of the particles can be non-regular, so that the surface is not a single continuous curve or so that the surface is not smooth.

The microspheres can be a mixture of different polymers and can also be a mixture of different particles, beads, or globules of different sizes. The agents can also have pores of different sizes.

At the very least, the agents should have the following properties:
1. They should be capable of forming multi-point contacts with cells or portions of cells thereof, such as the outer cell membrane and molecules on this membrane;
2. They should be able to promote ocular injury healing without significant chemical alteration or degradation; and
3. They should be substantially insoluble in aqueous media such as bodily fluids, and instead should form a suspension.

These characteristics are important because as discussed below, the effect of the agents of the present invention appears to be related to the formation of multipoint contacts between the material of the agents and a portion of the cell, such as the outer cell membrane, thereby forming an adherent surface to which the cells may attach. Such multipoint contacts are possible with many different polymers which permit charged groups to be accessible for interaction with molecules and portions of the outer cell membrane. Thus, although the description below focuses on one type of agent, microspheres, it is understood that the present invention covers any material capable of forming such multi-point contacts.

As noted above, preferably the microspheres have diameters in a range of from about 0.01 microns to about 200 microns, more preferably in a range of from about 1 to about 100 microns, and most preferably from about 2 to about 20 microns. The microsphere composition of the present invention has a pH between about 7-9. Without desiring to be bound by any mechanism, it should be noted that these preferred ranges are the best size for enabling uptake of the microspheres by macrophages infiltrating the wound area. The microspheres appear to actually attract and activate the macrophages through contact with at least a portion of the macrophages, probably the molecules of the outer cell membrane of the macrophage. The anti-inflammatory and anti-bacterial effects observed for the microspheres are thus presumably indirect effects, obtained through the activation of the macrophages or other cells.

Another important property of the microspheres is the charge of the surface groups. The overall charge carried by certain preferred examples of microspheres was measured as a Z or zeta potential by electrophoretic mobility (millivolts) by a ZetaMaster (Malvern Instruments, United Kingdom). Hereinafter, the term "charged" refers to a Z potential with an absolute value of at least about 1 mV, and preferably of at least about 10 mV, whether negative or positive.

The microspheres of the present invention are suspended in a liquid solution which can be applied conveniently to the eye. The microspheres are packaged in a sterile container under argon, neon, or nitrogen at an optimum pH and varying concentration and volume by conventional methods.

The microspheres in the suspensions tested did not aggregate, coalesce, clump, or undergo irreversible caking. Although the microspheres did settle somewhat over time, they were easily resuspended with gentle agitation.

For application to the eye as a suspension it is necessary that the microspheres be maintained in a suitable medium such that they do not form agglomerates during prolonged periods of storage at ambient temperatures. Acceptable suspension media should require merely gentle inversions following settling during the storage period.

The stability of suspensions intended for multiple doses is supported by the addition of preservatives which prevent potential microbiological growth. The preparations are prepared under aseptic conditions and aliquots of each material are exposed to the indicated microbiological organisms for four weeks and evaluated for growth as described in the U.S. Pharmacopeia.

Compositions with satisfactory particle sizes and stabilities may be prepared as unidose suspensions without preservatives. These compositions are satisfactory for ophthalmic uses when prepared under aseptic conditions and packaged in containers for single doses.

5.2 Pharmaceutical and Biologic Agents

As disclosed herein the compositions consisting of microspheres in a suitable vehicle may without further active ingredients promote ocular wound healing with concomitant anti-inflammatory effect. Nevertheless, it is to be understood that the beneficial effects of the microspheres may be enhanced, supplemented or complemented by one or more additional pharmaceutical agent.

Any one or more of the following kinds of pharmaceutical agents can be included in the prophylactic or therapeutic compositions together with the microspheres: antiseptics, antifungal agents, antiviral agents, antihistamines, antibiotics, anti-inflammatory agents, analgesics, minerals, vitamins.

Biologically active substances which can be included in the therapeutic composition include, but are not limited to, sulfonamides, proteolytic enzymes, antibiotics, anti-oxidants, amino acids, macrophage stimulating factors, anesthetics, cycloplegics, COX-2 inhibitors, or bradykinin antagonists combined with 21-amino steroids.

Growth and regulatory factors may be added to the therapeutic composition to aid in reepithelization of the ocular injury site. Such factors may include, but are not limited to, platelet-derived growth factor (PDGF), platelet-derived angiogenesis factor (PDAF), transforming growth factor-beta (TGFB), platelet factor (PF-4), alpha and beta fibroblast growth factors ($\alpha$FGF and $\beta$FGF), epidermal growth factor (EGF), and growth hormone (GH).

Platelet derived growth factors stimulate a cascade of systems involved in re-epithelization, and transforming growth factor-beta is a family of dimeric proteins which regulate the proliferation and differentiation of many cell types. (Massague, 1990, Ann. Rev. Cell. Biol. 6:597-619).

Ocular injuries, especially chemical burns, have a risk of necrosis and tissue damage by free radicals. Inclusion of antioxidants (e.g., vitamin E) and proteolytic enzymes or other agents (e.g., acetylcysteine or EDTA) could prove effective in preventing these conditions.

Epithelialization may also be increased by including trace elements (e.g., zinc, cobalt). Many enzymes are zinc dependent, most notably DNA-polymerase and reverse-transcriptase, which are required for epithelial proliferation. Low levels of zinc would be equivalent to depressed function of these enzymes. DNA-polymerase and reverse-transcriptase are required for epithelial proliferation. Vitamin B12, also called Cobalamin, contains an active cobalt group at the center of the enzyme. B12 deficiencies can lead to lesions in the optic nerve and impaired vision. Introduction of B12 and cobalt with microspheres could heal the nerve, which is epithelial in nature, and address the vitamin deficiency.

Vitamin A is necessary for epithelization and vision. A deficiency in vitamin A leads to a reduction in mucous secreting cells, such as those in the conjunctiva of the eye, and also to replacement of columnar epithelial cells with stratified epithelium in the corneal epithelium. Vitamin A is also important for vision by interacting with the rod cells of the eye. Introduction of vitamin A with the microspheres may promote epithelialization and in some cases, improve vision.

5.3 Ocular Injuries (A) Foreign Bodies

25% of all ocular injuries involve foreign bodies on the surface of the cornea. No scarring will occur if the injury affects only the corneal epithelium, but if it also affects the Bowman zone, scarring is possible. After removal of the foreign body, the eye is treated with a sulfonamide or antibiotic and, if there is ciliary congestion and photophobia, or if the removal of the foreign body was difficult, it is treated with a cycloplegic such as 5% homatropine. The therapeutic compositions of the present invention are designed to accelerate healing of the injury caused by the foreign body and to prevent infection, and to improve the clinical outcome.

(B) Chemical Burns

Chemical burns are treated by first diluting the chemical by flushing the eye with fluid, and then preventing infection through the use of topical antibiotics. Intraocular pressure may be reduced by applying timolol, epinephrine, acetazolamide, or other similar agents. If epithelialization of the cornea is incomplete after one week, there is a danger of stromal necrosis, in addition to the risk of infection. It is therefore critical that the healing be accelerated to reduces these risks.

Severe scarring is another common result of chemical burns. The therapeutic compositions of the present invention are designed to accelerate the healing of the corneal erosion caused by the chemical burns, to prevent stromal necrosis and infection of the eye, and to reduce corneal scarring and thereby restore/preserve corneal transparency.

Unexpectedly the compositions of the present invention are able to prevent or reduce scar formation while simultaneously enhancing ocular healing, wound repair and maintaining corneal transparency. While not wishing to be bound by any specific mechanism of action it appears that these beneficial effects can be obtained due to the anti-inflammatory actions of the compositions. It is emphasisized that the anti-inflammatory effects are obtained by the suspension of microspheres without additional medication.

(C) Lacerations

Lacerations of the cornea are followed by prolapse of the iris, which closes the injury. As in all eye injuries, there is a risk of infection. Lacerations may also extend to the sclera, which is a much more severe injury. In such a case, surgery is required to remove prolapsed uveal tissue from the injured area, and the sclera is closed with sutures. The therapeutic compositions of the present invention are designed to accelerate the healing of the laceration and to prevent infection.

(D) Traumatic, Toxic, Deficiency, and Hereditary Optic Neuropathies

Optic neuropathies affect the optic nerve, which may adversely affect vision. Traumatic optic neuropathies may be caused when the head is struck by an object, such as a ball, or if it is pierced by an object such as a bullet. Toxic optic neuropathies are caused by chemicals toxic to the optic nerve; a common example is the ingestion of methanol. Deficiency optic neuropathies can result from vitamin deficiencies such as a B12 deficiency, and may cause lesions in the optic nerve. Hereditary optic neuropathies can be caused by mutations in the nuclear or mitochondrial genomes. The therapeutic and prophylactic compounds of this invention could be used to heal the optic nerve and correct vitamin deficiencies. They may also create an environment which would reduce or prevent mutations in optic cell genomes.

(E) Inflammatory Conditions

Suspensions of microspheres may be used as an anti-inflammatory therapy of the eye, especially for treating inflammatory conditions of the ocular adnexa, palpebral or bulbar conjunctiva, cornea and anterior segment of the globe. Common therapeutic applications for anti-inflammatory suspensions of microspheres include viral, allergic conjunctivitis, acne rosacea, iritis and iridocyclitis. Microspheres may also be used to ameliorate inflammation associated with, corneal injury due to chemical or thermal burns, or penetration of foreign bodies. Such conditions may result from surgery, injury, allergy or infection to the eye and can cause severe discomfort.

Notably, microspheres have considerable therapeutic advantages in reducing inflammatory responses, compared to the prevalent topical ocular use of NSAI agents and corticosteroids. Use of topical steroids is associated with a number of complications, including posterior subcapsular cataract formation, elevation of intraocular pressure, secondary ocular infection, retardation of corneal wound healing, uveitis, mydriasis, transient ocular discomfort and ptosis. Numerous systemic complications also may arise from the topical ocular application of corticosteroids. These complications include adrenal insufficiency, Cushing's syndrome, peptic ulceration, osteoporosis, hypertension, muscle weakness or atrophy, inhibition of growth, diabetes, activation of infection, mood changes and delayed wound healing.

(F.) Ocular Surgical Applications

Compositions of microspheres in accordance with the present invention, may also be used to ameliorate inflammation associated with ocular surgery, and in this context are particularly useful in a prophylactic modality as well as in promoting healing and reducing scarring as has been detailed above.

Of particular suitability is the use of the compositions of the invention for: post-trabeculectomy (filtering surgery); post pterygium surgery; post ocular adnexa trauma and surgery; post intraocular surgery and specifically: post vitrectomy, post retinal detachment and post retinotomylectomy.

It will be appreciated by the artisan that these are intended to serve as non-limitative examples of prevalent surgical procedures for which the compositions and methods of the invention are useful.

6. EXAMPLES

Example 1

Effect of Microspheres on the Epithelialization of Corneal Erosions Caused by Chemical Burns The microspheres of the present invention were demonstrated to significantly reduce inflammatory reaction of eye caused by a severe chemical burn.

Chemical burns were produced by a standardized filter paper disc soaked with 5N NaOH applied onto the left eyes of six New Zealand albino adult rabbits (weight 2.5-3.5 kg), to test the effectiveness of the present invention. The wounds of the three control rabbits were treated with DMEM (vehicle control). The wounds of the three test rabbits were treated with Polyheal1, one particular embodiment of the present invention. Polyheal1 is composed of polystyrene microspheres with a size distribution 1-10 micron, when at least 80% of the particles ranged between 3-7 microns in diameter, in a concentration of $4.5 \times 10^6 \pm 25\%$, particles/mL. The solution has a pH between 7 and 9 with a zeta potential not higher than $-60$ mV. The osmolality is 320-354, the pyrogenicity is not more than 0.5 EU/ml, and the growth promotion potential is not less than 60% of the standard curve.

The eyes of each rabbit received 2 drops of either DMEM or Polyheal1, four times per day. The effects of the solutions on ocular injury healing were evaluated macroscopically on the basis of inflammatory response and clarity of the cornea.

Importantly, inflammatory responses elicited by the injury were significantly decreased in the test rabbits compared to controls.

This experiment demonstrates the utility of the compositions of the invention in acute alkali burn of the greatest severity. The clinical appearance of an eye of NZW rabbit 6 months of age after application of a 6 mm filter paper patch soaked in a 5 N alkali (ammonia) solution for 10 sec. was significantly improved after application of Polyheal1 versus control.

As presented in FIG. 1 the eyes of rabbits treated immediately after the burn with Polyheal1 (q.i.d) showed Perilimbal blanching, moderate chemosis, and corneal opacification are evident, yet the cornea show some clear islands (arrows) and the conjunctiva and the ocular adnexa are moderately inflamed.

Figure 2:
FIG. 2 shows the control rabbit group, on the fourth day after the chemical burn was induced. The control rabbits were treated with the vehicle DMEM.

In comparison as can be seen in FIG. 2 the eye of rabbits treated with the control vehicle (Polyheal vehicle medium) show Perilimbal blanching, severe chemosis, and total corneal opacification are seen and in addition it is evident that the conjunctiva and the ocular adnexa are ulcerative and severely inflamed.

Example 2

Eye Irritation Test

Acute Eye Irritation/Corrosion in the Rabbit

OECD Guideline for the Testing of Chemicals, Section 4, No. 405, "Acute Eye Irritation/Corrosion", adopted Feb. 24, 1987, Draft Revised Guideline 405, March 2000. Assessment of the potential of the Test Item POLYHEAL 1 and ×10 Polyheal 1 to produce eye irritation/corrosion by single dose ocular instillation and limited exposure of the anterior surface of the rabbit eye, thereby providing information on health hazards likely to arise from its exposure under conditions of its projected use as a wound healing stimulator.

Test System:

Six female (New Zealand White rabbits, weight not less than 2.5-3.5 kg) were divided on two groups. 3 animals were treated with Polyheal 1 and other 3—with ten-fold concentrated microspheres suspension.

Pre-Test Preparations of Animals:

Approximately 24 hours before dosing, both eyes of each test animal provisionally assigned to testing are examined. Animals showing eye irritation, ocular defects or pre-existing corneal injury are excluded from the study.

Initial Test: The test is conducted in a sequential testing strategy, using one animal. If the results of this test indicate the substance to be corrosive or a severe irritant to the eye, further testing is not performed.

Confirmatory Test:

If the initial test does not show corrosive effects the negative response is confirmed in two additional animals.

If an irritant effect is observed in the initial test, continuation is as well, in a sequential manner, using one animal, rather than exposing the two additional animals simultaneously. If the second animal reveals corrosive of severe irritant effects, the test is not continued.

Application of the Test Item:

The Test Item is placed in the conjunctival sac of the right eye of each animal, after gently pulling the lower lid away from the eyeball. The lids are then gently held together for about a second in order to prevent loss of the applied material. The untreated left eye serves as control.

Irrigation:

The eyes of the test animals are not washed out for 24 hours following instillation of the Test Item. If immediate corrosive or irritating effects are observed in the first animal after instillation of the Test Item, appropriate washout conditions are applied. In this event, the treated eye of the rabbit is washed with sterile physiological saline solution, using a volume and velocity of flow, which will not cause any injury.

Clinical Observations and Grading of Eye Reactions:

The final evaluation of the Test Item's potential irrigation effects is based on a daily calculation of the average of each of the following irrigation parameters in all three animals: Average opacity for each day; average iritis for each day; average redness for each day; and average chemosis for each day.

The Test Item is classified as irritant if the average score at any of the grading times is any of the following: Cornea 2.0; Iris 1.0; Redness 2.5; and Chemosis 2.5.

The grades for different ocular lesions were scored as follows:

CORNEA: Opacity, degree of opacity (readings are taken from the most dense area);

No ulceration or opacity;

Scattered or diffuse areas of opacity (other than slight dulling of normal luster) details of iris clearly visible;

Easily discernible translucent area; details of iris slightly obscured Nacrous area; no details of iris visible; size of pupil barely discernible Opaque cornea; iris not discernible through the opacity.

IRIS: Normal

Markedly deepened rugae, congestion, swelling, moderate circumcorneal hyperemia; or injection; any of these or combination of any thereof, iris reactive to light (a sluggish reaction is considered to be an effect); Hemorrhage, gross destruction, or no reaction to light (any or all of these).

CONJUNCTIVAE: Redness; refers to palpebral and bulbular conjunctivae; excluding cornea and iris Normal Some blood vessels hyperemic (injected)

Diffuse, crimson color; individual vessels not easily discernible Diffuse beefy red.

CHEMOSIS: Swelling refers to lids and/or nictitating membranes

Normal

Some swelling above normal

Obvious swelling, with partial eversion of lids

Swelling with lids about half closed

Swelling with lids more than half closed.

Ocular Reactions:

Reactions of eye irritation are examined at: 1, 24, 48 and 72 hours after instillation of the Test Item. If there is no evidence of irritation at the 72-hour examination, the study is terminated.

Following ocular exposure, regular checks (once daily) were carried out to ensure that test animals do not show significant or extended distress.

No treatment related ocular reactions were noticed immediately following instillation. None of the animals revealed ocular irritation effect throughout the entire 72-hr observation period. It is therefore concluded that the Polyheal 1 and ten fold concentrated Polyheal 1 may be classified as non irritant to the eyes.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

What is claimed is:

1. A method of reducing inflammatory reaction of the eye caused by a severe chemical burn, said method comprising administering to the injured inflamed eye an effective amount of a composition comprising:

a pharmaceutically acceptable carrier having a pH between 7 and 9; and about 0.001-25% by weight of microspheres in suspension in said pharmaceutically acceptable carrier, said microspheres having varying diameters in the range of about 0.01 μm to about 200 μm, said microspheres being capable of forming multi-point contacts with a cellular membrane and said microspheres being substantially non-biodegradable during the period of therapy, wherein said microspheres lack the inclusion of any other drug or therapeutic substance, wherein said composition consists of polystyrene microspheres with a size distribution 1-10 micron, with at least 80% of the particles being ranged between 3-7 microns in diameter, in a concentration of $4.5 \times 10^6 \pm 25\%$ particles/ml, the composition having a pH between 7 and 9, with a zeta potential not higher than −60 mV, an osmolality of 320-354, and a pyrogenicity of not more than 0.5 EU/ml.

2. The method according to claim 1, wherein said pharmaceutically acceptable carrier is an aqueous medium.

3. The method according to claim 1, wherein the composition further includes a therapeutic agent added thereto.

4. The method according to claim 1, wherein the composition further includes a preservative added thereto.

* * * * *